United States Patent [19]

Goodman

[11] Patent Number: 5,551,326
[45] Date of Patent: Sep. 3, 1996

[54] ADHESIVE-LESS MICROTOME BOAT

[75] Inventor: Steven L. Goodman, Madison, Wis.

[73] Assignee: Wisconsin Alumni Research Foundation, Madison, Wis.

[21] Appl. No.: 356,422

[22] Filed: Dec. 15, 1994

[51] Int. Cl.⁶ .................................................. G01N 1/06
[52] U.S. Cl. .............................. 83/167; 83/171; 83/915.5
[58] Field of Search ................................ 83/915.5, 170, 83/171, 167; 62/320, 331; 403/34, 35, 387

[56] References Cited

U.S. PATENT DOCUMENTS

| D. 251,259 | 3/1979 | Converse, Jr. | 83/915.5 X |
|---|---|---|---|
| 3,103,844 | 9/1963 | Persson | 83/167 X |
| 3,225,639 | 12/1965 | Martinelli | 83/915.5 X |
| 3,377,898 | 4/1968 | Persson | 83/915.5 X |
| 3,540,335 | 11/1970 | Sitte | 83/915.5 X |
| 3,699,830 | 10/1972 | Pickett | 83/915.5 X |
| 3,832,923 | 9/1974 | Lassmann et al. | 83/170 X |
| 3,924,500 | 12/1975 | Kindel | 83/915.5 X |
| 4,207,790 | 6/1980 | Endo | 83/915.5 X |
| 4,221,146 | 9/1980 | Kindel et al. | 83/915.5 X |

OTHER PUBLICATIONS

Ultramicrotomy catalog pp. 28, 29, 100, 56, 75, admitted prior art (undated).

*Primary Examiner*—Rinaldi I. Rada
*Assistant Examiner*—Boyer D. Ashley
*Attorney, Agent, or Firm*—Quarles & Brady

[57] ABSTRACT

A boat for use with microtomes eliminates the needs for adhesives and provides reusability by use of an elastomeric gasket compressed between contacting surfaces of the knife and boat. The compression is provided by a clamping action of components of the boat for ultramicrotome applications or in the case of histological knives, where the knife base is much broader, by means of a separate leaf spring encircling the unobstructed lower edge of the knife.

8 Claims, 3 Drawing Sheets

ADHESIVE-LESS MICROTOME BOAT

FIELD OF THE INVENTION

This invention relates generally to microtome equipment used to cut thin sections of material for microscopic examination and, in particular, to a boat that may be attached to a microtome knife for receiving sliced sections.

BACKGROUND ART

Microtomes are precision mechanical knives used to cut extremely thin sections of specimens for microscopic study. In light microscopy (LM), thin sections are required to produce a specimen conforming with the thin depth of field offered at high magnification by optical instruments. Thin sections also aid in the transmission of light through the specimen to be received by the objective lens of the microscope. Sections may be approximately 1 to 100 microns thick and about 30 mm wide.

Thin sections may also be prepared for electron microscopy. With transmission electron microscopy (TEM), the thin sections aid in the transmission of a sufficient flux of electrons through the specimen to form the image. In the case of scanning electron microscopy (SEM) where depth of field is greater and no transmission of electrons is required, a section or series of sections may nevertheless be used to reveal internal structure. Sections for electron microscopy are prepared with an "ultramicrotome" and may be approximately 40 nm thick and approximately 0.5 mm wide.

In either case, with either a microtome or an ultramicrotome, the samples are normally first embedded in a supporting matrix, impregnated with a supporting material such as a hard plastic, or frozen to make sectioning easier. The prepared sample is then placed in a collet which moves up and down across a microtome knife, the collet advancing toward the cutting plane of the knife after each pass, the amount of advance determining the section thickness.

For light microscopy, the microtome knife may be the sharpened edge of a steel plate, (a "histology" knife) or a fractured edge of a glass plate of similar dimension, (a Ralph knife). For electron microscopy, glass, diamond, and sapphire knives are used.

The extremely slim sections produced by an ultramicrotome require careful handling. In order to facilitate removal of these sections from the knife, it is known in the art to construct a boat that provides a liquid filled trough fitting against the side of the knife from which the section will be dislodged. The liquid in the boat, which may be water or a solvent such as alcohol or acetone, causes the section to float on its surface as a result of buoyancy or surface tension, adhering by one edge to the knife or the previous section. From here, the section may be removed by a fine brush or the like, having been prevented from adhering over its entire surface to the knife blade itself. For TEM, the section is picked up directly by the TEM grid.

With a carefully designed boat, a multiple series of sections can be cut which form a floating chain on the surface of the liquid that may be removed in one piece so as to provide a set of sections of known relationship to each other.

The more expensive knives for ultramicrotomy, such as diamond knives, come glued to a fixture that includes a boat. These knives are relatively long-lived and hence a permanently attached boat is practical.

For glass knives, boats are constructed as they are needed, by the operator of the microtome, using materials at hand. The glass knives used with electron microscopy are generally triangular plates where the width of the plate at one vertex provides the cutting edge. A boat may be formed for these knives by loosely wrapping a single turn of an aluminized Mylar tape about the cutting apex. Gaps may be filled with wax or lacquer. The tape must be trimmed carefully around the knife blade so as not to interfere with the operation of the microtome and without damaging the extremely precise edge of the knife. The construction of such boats is not only time consuming but often the end product is irregular in dimension and produces a liquid surface that pulls the sections to one side where they adhere to the wall of the boat.

These problems are addressed in part by commercially available plastic boats sized to abut one face of the knife and to be attached to the knife with lacquer or wax. Such boats provide a uniform and symmetrical liquid surface on which to receive the sections. Nevertheless, such boats are time consuming to install. The adhesives commonly used to attach such boats to the knives can contaminate the liquid contained in the boat adversely affecting, for example, the way the sections take stain. Normally, the adhesive prevents the boats from being removed for reuse.

Boats are not normally used with the histology or Ralph knives of microtomes but rather these knives are manually wetted with a water or a water-alcohol mixture to minimize adhesion of the section to the knife and to aid in removal of the individual sections as they are cut.

SUMMARY OF THE INVENTION

The present invention provides a boat that may be quickly attached to a microtome or ultramicrotome knife without the need for adhesives. Adhesive-less sealing is provided by an elastomeric material, placed at the contact surfaces between the boat and knife, that deforms under light pressure to seal the boat to the knife. The boat is constructed to provide a light compressive force to these surfaces.

Specifically, the boat includes two upstanding opposed sidewalls that are both spaced apart and joined at their rear edges by an upstanding rear wall. The rear wall has a lower edge shaped to fit against an upper surface of the knife, at a first interface, when front portions of the upstanding sidewalls are aligned with the cutting edge of the knife with the upstanding sidewalls abutting the knife at second and third interfaces, respectively. When the knife is so positioned, the knife forms a fourth wall joining the front edges of the upstanding sidewalls to create an upwardly open trough. An elastomeric sealing material is positioned on the upstanding sidewalls at the second and third interface and at the rear wall at the first interface so as to create a releasable water tight seal between the knife and the upstanding walls and the rear wall when the upstanding sidewalls are compressed against the knife at the first and second interfaces with a predetermined force.

The compressing force may be provided by a separate clamp between the sidewalls and the knife or may be produced by configuring the boat so that the natural flexure of the material of the walls of the boat, when deformed to accommodate the knife, clamp the boat to the knife.

Thus, it is one object of the invention to provide a microtome boat that eliminates adhesives and potential contaminants from such adhesives.

Eliminating adhesives greatly speeds the process of attaching the boat to the knife and permits the boat to be removed from the knife after use.

Thus, it is another object of the invention to provide a boat for microtomes and ultramicrotomes that is easy to install and that is reusable.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
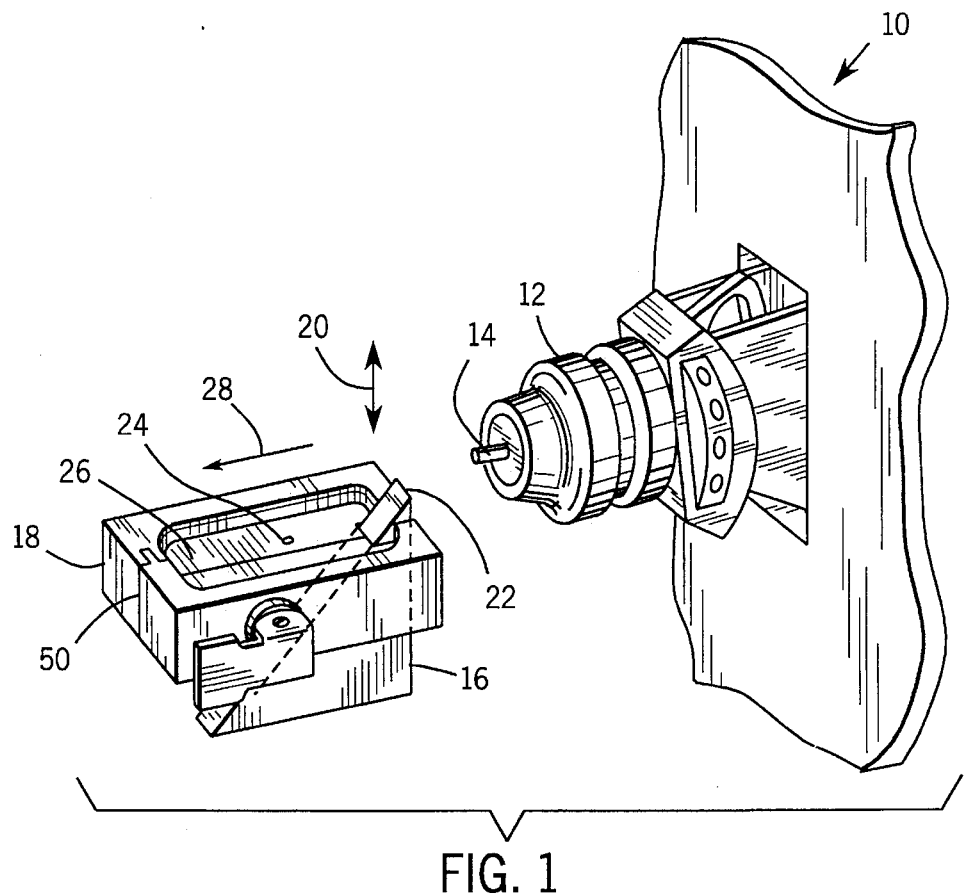
FIG. 1 is a perspective view of a specimen holder for an ultramicrotome positioned above a glass knife, the latter which is held within a two-part boat of the present invention.

Referring to FIG. 1, an ultramicrotome 10 includes a specimen holder 12 holding a specimen 14 embedded in a supporting plastic matrix. Beneath the specimen 14 is a glass knife 16 held within boat 18 as will be described in detail below.

During operation of the ultramicrotome 10, the specimen holder 12 moves downward along vertical axis 20 to cross the upwardly facing knife edge 22 of the glass knife 16 thereby removing a section 24 from the specimen 14. The section 24 is drawn from the knife edge 22 down onto the surface of a liquid 26 contained within the boat 18. The liquid surface rises substantially to the knife edge 22 so as to float the section 24 away from the knife edge 22 preventing it from adhering, except at a single edge, to the knife 16.

After completion of its downward stroke along axis 20, the specimen holder 12 reverses direction and moves upward. Then, at the top of its stroke, the specimen holder 12 advances along specimen axis 28 by an amount equal to the desired thickness of the section 24. This process is repeated with the specimen holder 12 moving down past the specimen 14 across the knife edge 22.

Figure 2:
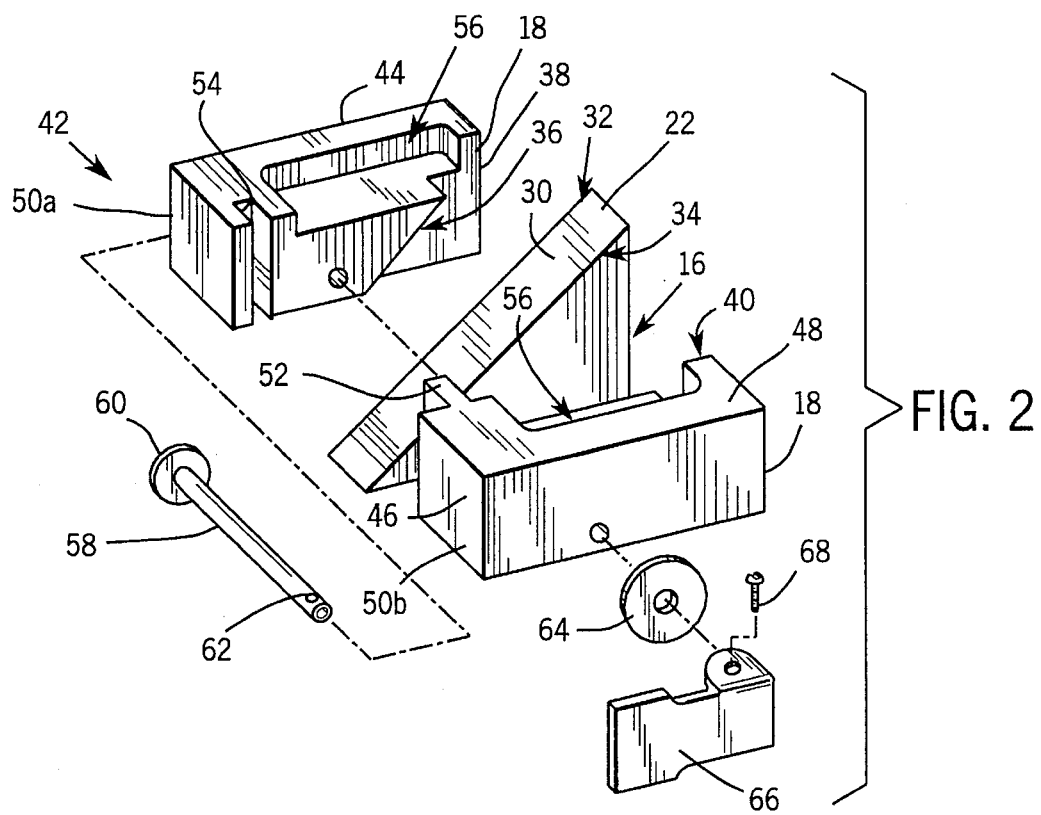
FIG. 2 is an exploded perspective view of the two-part boat and the glass knife of FIG. 1 showing the interface between the two-part boat and a clamp holding the boat against the knife.

Referring also to FIG. 2, the knife 16 is a right-triangular prism made by fracturing a square tile of glass along a diagonal across the square. The knife edge 22 so produced extends across the width of the tile at a vertex of the knife 16.

The knife 16 is positioned so that a vertical edge of the triangle is adjacent to the specimen 14 (and generally aligned with the vertical axis 20) and a lower edge of the triangle is horizontal to be aligned with specimen axis 28. The hypotenuse of the triangle of the knife 16 thus extends downward from the cutting edge 22 away from the specimen 14. This hypotenuse forms an upper surface 30 of the knife 16, on the side where cut sections 24 fall from the knife edge 22, and is flanked by a right and left side 34 and 32, respectively, formed by the parallel faces of the knife 16.

The boat 18 surrounds the upper half of the knife 16 on its three surfaces 30, 34, and 32 and may be constructed in two parts which clamp about the knife 16 to contact the upper surface 30 of the knife 16 at a first interface 36, the left side 32 of the knife at a second interface 38, and the right side 34 at a third interface 40. Generally, each of these interfaces is planar thus matching the corresponding planar faces of the knife 16. The lower half of the knife 16 remains exposed so as to be mounted in the microtome (not shown).

A left half 42 of the boat 18 includes an upstanding sidewall 44 providing the interface surface 38 that fits against side 32 of the knife 16. Likewise, the right half of the boat 46 includes an upstanding sidewall 48 that provides the interface surface 40 that contacts the right side 34 of the knife 16. A rear wall 50 joins the rear edges of sidewalls 44 and 48 and provides the first interface surface 36.

In the embodiment of FIG. 2, rear wall 50 is constructed of two halves 50(a) and 50(b) where 50(a) is attached to left sidewall 44 and 50(b) is attached to right sidewall 48. A tongue 52 extending outward from the rear wall 50(b) for the height of the rear wall 50(b) toward the rear wall 50(a) is received by a correspondingly sized groove 54 in rear wall 50(a) when the boat halves 42 and 46 are placed together about the knife 16.

When the halves 42 and 46 of the boat are assembled about the knife 16, surfaces 32, 30 and 34 of the knife contact walls 44, 50 and 48, respectively. Interface surface 36 forms a diagonal lower portion of the rear wall 50 and fits against the upper surface 30 of the knife 16.

Each of boat halves 42 and 46 provide a half pocket in their upper surfaces which when the boat halves 42 and 46 are assembled together about the knife 16 form a trough 56 that may hold the liquid 26. The three of the four side walls of the trough 56 are provided by the sidewalls 44 and 48, and rear wall 50. The front wall of the trough is provided by the upper diagonal surface 30 of the knife 16 itself. In this way the liquid in the trough 56 may come arbitrarily close to the knife edge 22.

The bottom of the trough 56 is provided by portions of the side and rear walls 44, 48 and 50 which extend out over the upper surface 30 of the knife 16.

The halves 42 and 46 of the boat 18 may be held together about the knife 16 by means of a pin 58 passing through and joining both of the sidewalls 44 and 48. The pin 58 has a head 60 at one end and a radial hole 62 cut through its shaft at the other end. The pin 58 is inserted through a hole passing through the sidewall 44, a front portion of the rear wall 50 and the sidewall 48 along a transverse axis so that the head 60 abuts the outer left surface of the upstanding sidewall 44 and the radial hole 62 projects out from the right surface of the upstanding sidewall 48. There the pin 58 passes through a washer 64 and is received by a thumb cam 66 which may pivot about the axis of the radial hole 62, turning about a dowel 68 inserted through the thumb cam 66 and the radial hole 62. The hole in the thumb cam 66 is cut eccentrically so that rotation of the thumb cam 66 compresses a camming surface of the thumb cam 66 against the washer 64 on one side of the boat 18 forcing the dowel 68 and the pin 58 further out from the sidewall 48. This draws the head 60 inward pulling the halves 42 and 46 of the boat 18 closer together.

In the preferred embodiment, the boat halves 42 and 46 are constructed of a polymeric elastomer such as styrene-butadiene-rubber or other thermoplastic elastomers so that interface surfaces 38 and 40 deform to seal against the sides 32 and 34 of the knife 16 under compression action of the thumb cam 66 and pin 58. A downward pressure on the boat halves 42 and 46 against the upper surface 30 of the knife 16 at the time of clamping provides a similar compressive force between interface 36 and the upper surface 30 of the knife 16. This downward compressive force is retained against slippage upward of the boat 18 by the frictional contact between the interface surfaces 38 and 40 of the upstanding sidewalls 44 and 48.

Thus, a water tight trough 56 is formed having one side formed by the knife 16 and thus permitting the water surface to closely approach the knife edge 22 without intervening plastic material and without the need for adhesives such as may contaminate specimens. Because the components of the boat 18 can be entirely elastomeric and may be grasped by portions removed from the knife edge 22, the risk of damage to the knife edge is minimized.

Figure 3:
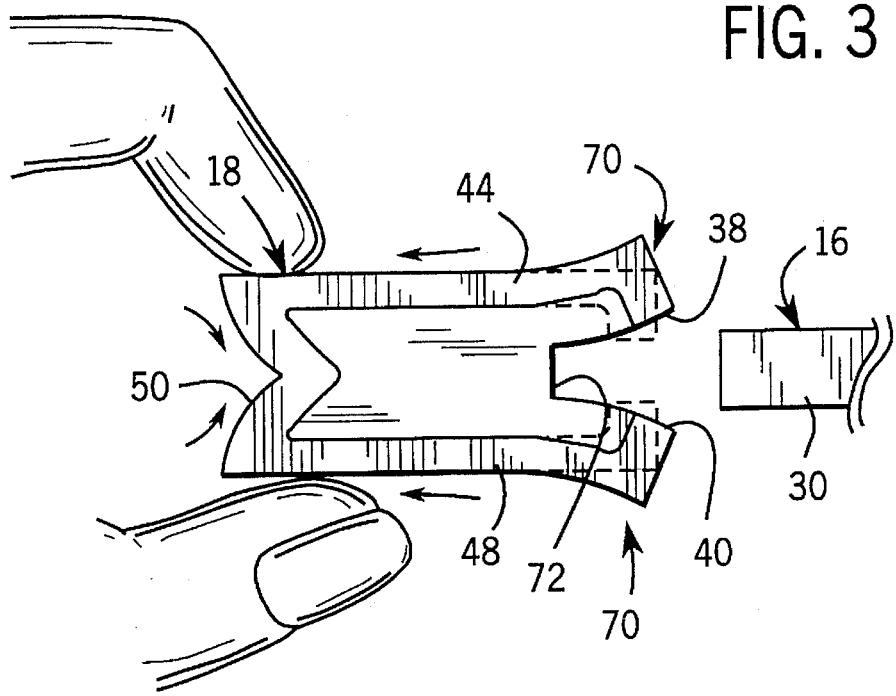
FIG. 3 is a view of an alternative embodiment of the invention employing a single piece boat design where the walls of the boat are held against the knife by the force of elastic deformation of the walls.

Referring to FIG. 3, in an alternative embodiment, the entire boat 18 may be constructed of an elastomeric material permitting the clamp of pin 58 to be eliminated. In this embodiment, the flexure outward of the sidewalls 44 and 48 to admit the knife 16 provides the necessary compressive force against the knife 16 deforming the very elastomeric material of the boat 18 to provide a liquid-tight seal.

In the embodiment of FIG. 3, the boat 18 is constructed of a single piece with the bottom of the trough 56 being substantially continuous between sidewalls 44 and 48 thereby providing a transverse span of elastomeric material largely resisting the separation of the sidewalls 44 and 48. Front edges 70 of the left and right sidewalls 44 and 48 are permitted to deform somewhat by an effective slot 72 produced by the space occupied by the upper surface of the knife 16. Here, insertion of the boat onto the knife involves a simple spreading of the front edges 70 of upstanding sidewalls 44 and 48 to receive the knife 16. The broad areas of the interface surfaces 38, 40 and 36 (not shown in FIG. 5) resists leakage of the contained liquid.

The rear wall 50 may be molded to be concave inward toward the center of the trough 56 so that pressure at the rear of the boat compressing the rear edges of the upstanding sidewalls 44 and 48 together, between, for example, the thumb and forefinger, folds the rear wall and serves to spread the front edges 70 of the upstanding sidewalls 44 and 48 apart to receive the knife in what may be a one-handed operation.

The thickness of the sidewalls 44 and 48 is adjusted so that proper elastic force is provided against the knife 16 to deform the elastomeric material to the surface of the knife 16. The embodiment of FIG. 3 is otherwise the same as the embodiment described with respect to FIG. 2.

Figure 4:
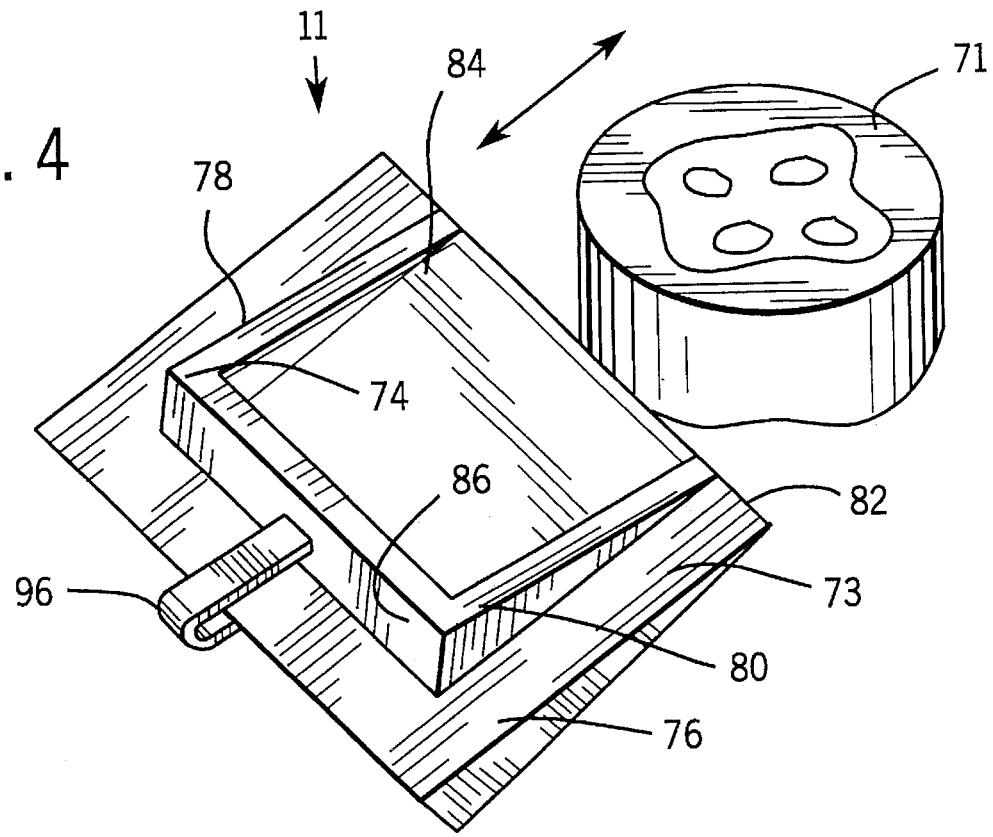
FIG. 4 is a perspective view of an encapsulated microtome specimen for a sliding microtome positioned in front of a histological knife on which a third embodiment of the boat of the present invention has been attached.

Referring to FIG. 4, a microtome 11 removes sections of a larger specimen 71 by means of a steel histological knife 73 (shown) or glass Ralph knife of similar dimension. The thicker sections produced by the microtomes 11 are at less risk of damage but are prone to roll up or fold. The adhesive-less design of the present invention makes the use of a boat with the larger knives of microtomes practical, and such a boat may reduce folding and rolling of the sections.

Figure 5:
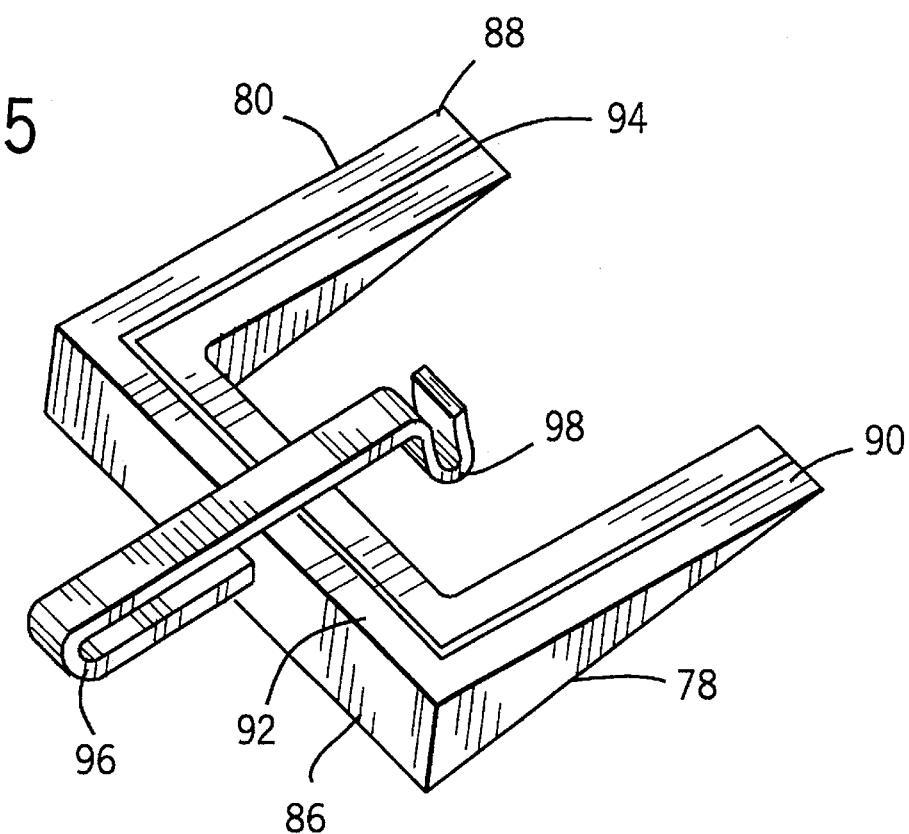
FIG. 5 is a perspective view of the inverted boat of FIG. 6 showing a C-shaped spring that presses the boat to the knife and showing the placement of an elastomeric gasket at the interface surfaces between the knife and boat.

Referring also to FIG. 5 the microtome boat 74 is constructed to fit against the upper surface 76 of the knife 73. Accordingly, the left and right upstanding walls 78 and 80 are generally triangular in vertical section tapering to an apex at the cutting edge 82 of the knife 73. The taper generally matches the difference between the horizontal surface of the liquid 84 contained within the boat 74 and the slope of the upper surface 76 of the knife 73. The rear edges of the upstanding sidewalls 78 and 80 are joined by a rear wall 86 so as to form a generally C-shaped structure open towards the specimen 71.

The lower surface of the left and right sidewalls 78 and 80 provide interface surfaces 88 and 90, respectively, whereas the lower surface of rear wall 86 provides interface surface 92. Each of interface surfaces 88, 90 and 92 in this embodiment are coplanar and may be lined with a gasket 94 constructed of an elastomeric material such as a silicone rubber strip. Downward force by the boat against the upper surface 76 of the knife 73, necessary to provide sealing by the elastomeric gasket 94, is provided by means of a C-shaped metal leaf spring 96 having one end attached to the rear wall 86 to extend rearwardly around the rear edge of the knife 73 and then upward against the underside of the knife 73 terminating in a finger 98 approximately centered within the area of the boat 74 but beneath the knife 73 to generally provide even compression of the gasket 94 over its entire length. It will be understood that other means of compression for example, a C-clamp may be used with a possible decrease in ease of use.

Figure 6:
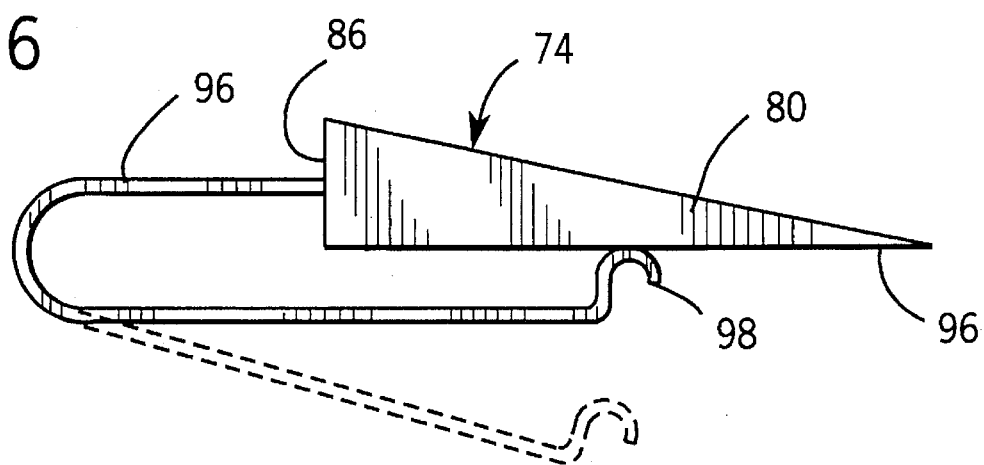
FIG. 6 is a side elevation of the boat of FIG. 4 showing the positioning of the C-shaped spring to provide a centered compressional force on the boat to seal the gasket against the knife.

Referring now to FIG. 6, the boat 74 of this embodiment is placed onto the knife 73 by moving the finger 98 downward away from the walls 78, 80 and 86 so as to accommodate the rear edge of knife 73. The boat 74 is then slid onto the knife 73 from back to front thereby keeping the operator's fingers from the area of the edge 82 of the knife 73. The spring force of spring 96 is selected to provide suitable compression of the elastomeric gasket 94.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

I claim:

1. A reusable microtome boat that may be attached to a microtome knife, the knife having an upper surface, an upper edge of the upper surface forming a cutting edge, the boat comprising:

(a) two upstanding, opposed, and spaced apart sidewalls having oppositely facing front and rear edges, each side wall forming an interface surface, the side walls joined at the rear edges by an upstanding rear wall, the rear wall having a lower edge shaped to fit against the upper surface of the knife at a first interface spaced apart from the cutting edge when the front edges of the upstanding sidewalls are positioned adjacent the cutting edge of the knife and the interface surfaces abut the knife at second and third spaced apart interfaces, respectively, so that the upper surface of the knife forms a fourth wall joining the front edges of the upstanding sidewalls, the rear wall, side walls and upper surface together forming an upwardly open trough;

(b) a compression means for urging the upstanding sidewalls against the knife at the second and third interfaces with a predetermined force; and (c) an elastomeric sealing material positioned on the two upstanding side walls at the second and third interfaces and on the rear wall at the first interface so as to create a releasable liquid tight seal between the knife and the upstanding walls and the rear wall when the upstanding side walls are held against the knife by the force.

2. The microtome boat of claim 1 wherein the upper surface of the knife is a planar upper surface and the knife includes two oppositely facing side surfaces which flank the upper surface and are perpendicular to the planar upper surface and wherein the second and third interfaces between the knife and the upstanding sidewalls of the boat are perpendicular to the first interface between the knife and the rear wall of the boat.

3. The microtome boat of claim 2 wherein the sidewalls are constructed of an elastomeric material and wherein the predetermined force of the compression means is provided by the elastic deformation of the upstanding sidewalls apart to receive the knife.

4. The microtome boat of claim 2 wherein the sidewalls and rear wall are constructed of an elastomeric material that forms the elastomeric sealing material at the first, second, and third interfaces.

5. The microtome boat of claim 1 wherein the compression means is a mechanical clamp drawing the upstanding sidewalls together about the knife.

6. The microtome boat of claim 1 wherein the first, second and third interfaces are between an upper planar surface of the knife and the rear wall and the upstanding sidewalls of the boat, respectively, and wherein the compression means is a C-shaped metal spring having one end positioned to press against a planar lower surface of the knife and the other end attached to the upstanding sidewalls and rear wall to press them downward against the planar upper surface of the knife when the boat is attached to the knife.

7. The microtome boat of claim 6 wherein the sidewalls and rear wall are constructed of an elastomeric material that forms the elastomeric sealing material at the first, second, and third interfaces.

8. A microtome boat that may be attached to a microtome knife, the knife having a planar upper surface flanked by two side surfaces perpendicular to the planar upper surface and a cutting edge, the boat comprising:

(a) two upstanding and opposed sidewalls spaced apart and joined at rear edges by an upstanding rear wall, the rear wall having a lower edge shaped to fit against the upper surface of the knife at a first interface when front edges of the upstanding sidewalls are aligned with the cutting edge of the knife and the upstanding sidewalls abut the knife at second and third interfaces, respectively, the second and third interfaces being perpendicular to the first interface between the knife and the rear wall of the boat, the upper surface of the knife forming a fourth wall joining the front edges of the upstanding side walls to create and upwardly open trough; and (b) a compression means for urging the upstanding sidewalls against the knife at the second and third interfaces with a predetermined force;

(c) wherein the side walls and rear wall are constructed of an elastomeric material that forms the elastomeric sealing material at the first, second and third interfaces.

* * * * *